United States Patent [19]

Osborn

[11] Patent Number: 4,964,857
[45] Date of Patent: Oct. 23, 1990

[54] BIODEGRADABLE DISPOSABLE DIAPER

[76] Inventor: Charles Osborn, R.R. 4, Box 155, Waxahachie, Tex. 75165

[21] Appl. No.: 425,130

[22] Filed: Oct. 23, 1989

[51] Int. Cl.5 ............................................. A61F 13/15
[52] U.S. Cl. ................................. 604/395; 604/397; 604/358
[58] Field of Search ................ 604/395, 397, 358, 393

[56] References Cited

U.S. PATENT DOCUMENTS

| | | | |
|---|---|---|---|
| 2,450,059 | 9/1948 | Rickerson | 604/397 |
| 3,563,242 | 2/1971 | Hedstrom . | |
| 3,593,716 | 7/1971 | Vogt . | |
| 3,874,385 | 4/1975 | Gellert . | |
| 4,036,234 | 7/1977 | Ishizuka . | |
| 4,072,150 | 2/1978 | Glassman . | |
| 4,265,245 | 3/1979 | Glassman | 604/397 |
| 4,417,894 | 11/1983 | Morris . | |
| 4,671,793 | 6/1987 | Hults et al. . | |
| 4,681,577 | 7/1987 | Stern et al. . | |
| 4,685,916 | 8/1987 | Enloe . | |
| 4,695,278 | 9/1987 | Lawson . | |
| 4,772,282 | 9/1988 | Oakley . | |

Primary Examiner—Randall L. Green
Assistant Examiner—Robert Clarke
Attorney, Agent, or Firm—Gregory W. Carr

[57] ABSTRACT

The present invention relates to an improved disposable diaper that is biodegradable, sanitary and environmentally safe. In general, the improved diaper has a removable inner sheet of material disposed of by flushing in a toilet or water closet. The remainder of the diaper is made of a biodegradable material that is disposed of in a conventional landfill.

15 Claims, 3 Drawing Sheets

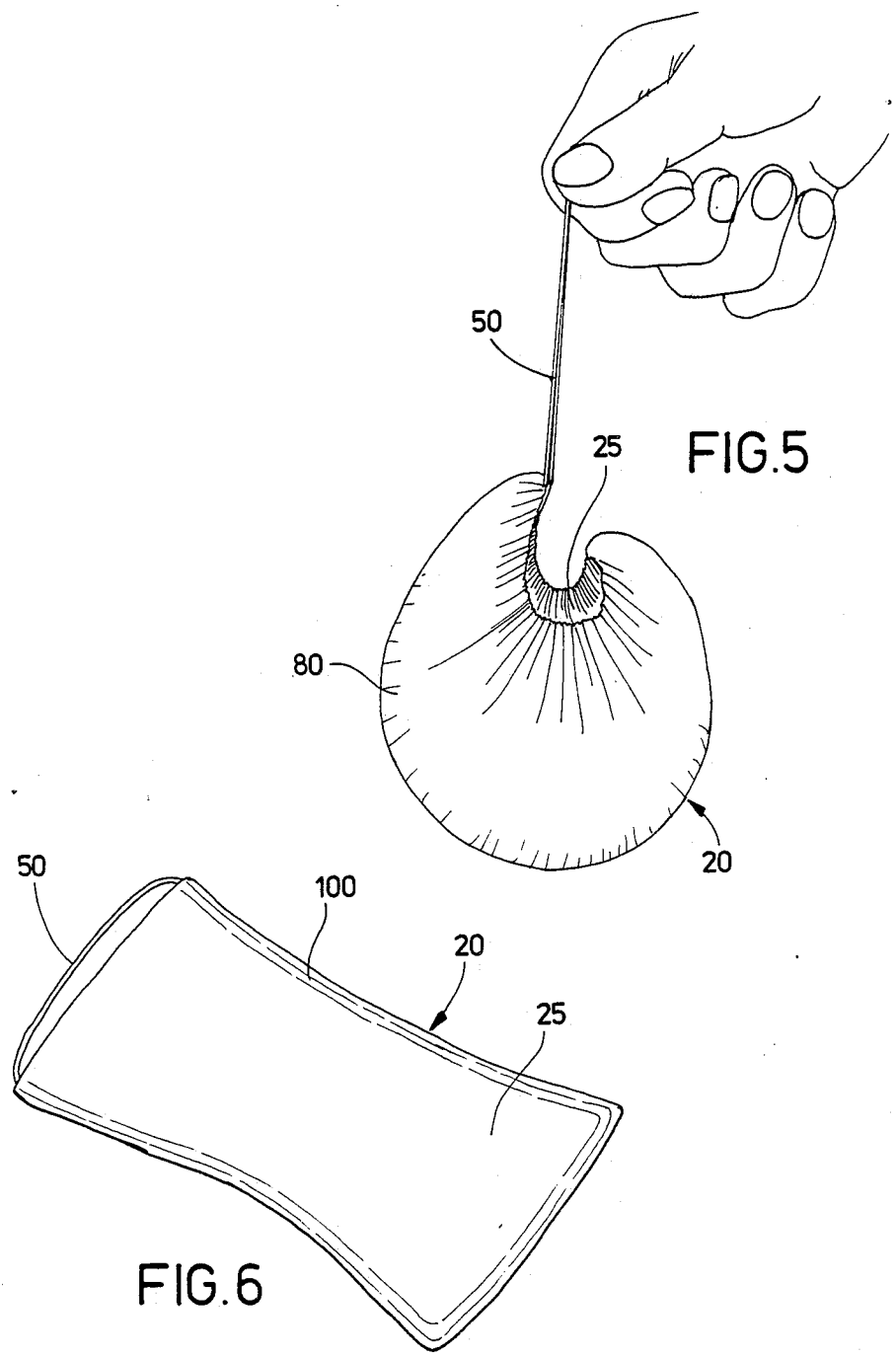

BIODEGRADABLE DISPOSABLE DIAPER

TECHNICAL FIELD

The present invention relates to an improved disposable diaper and in particular to a disposable diaper that is biodegradable and environmentally safe.

BACKGROUND OF THE INVENTION

Since the beginning of modern civilization, parents of infants have sought a solution to the time consuming and often messy proposition of disposing of soiled diapers.

The first diapers utilized by parents included cloth diapers, normally made of cotton, that had to be cleaned, washed and pressed for reuse. Needless to say this was a very inefficient and displeasurable task.

In the early 1960's disposable diapers made of an absorbant material were introduced into the market place. While these early disposable diapers alleviated some of the problems associated with cloth diapers, they required the use of waterproof panties to prevent moisture from soaking through to the outside.

In the 1970's improvements in disposable diapers revolutionized the diapering of infants. As the term "disposable" implies, these diapers were designed to be discarded after a single use. Such disposable diapers generally consisted of an absorbant pad, a liquid Permeable top sheet covering the pad and a liquid impervious back sheet for containing the liquid waste within the absorbant pad.

Not all disposable diapers, however, included all of the above features. For example some disposable diapers contained no back sheet and were used in conjunction with a separate pair of liquid impervious pants. Other disposable diapers utilized a variety of pad-like inserts for use with specially designed pants or for application within a conventional cloth diaper. Typical inserts are described in U.S. Pat. Nos. 2,450,059 and 20,023.

In the past few years, however, disposable diapers have been further improved. These improved disposable diapers normally have better absorption and water retention properties than the earlier disposable diapers. Such diapers are described in U.S. Pat. Nos. 4,685,916 and 4,695,278.

In eliminating many of the problems associated with earlier diapers, however, the improved disposable diapers have created new problems of their own. In particular such diapers have caused serious environmental and sanitary hazards. Such disposable diapers have created the environmentally unsafe practice of disposing of the plastic back sheet material in landfills. Such plastic materials have a biodegradable life of approximately five hundred (500) years. With the ever increasing use of landfills to contain today's ever growing volume of garbage it is both environmentally unsafe and practically unreasonable to store such materials for a five hundred (500) year time period.

A more pressing problem than the environmental landfill nightmare, however, is the unsanitary health conditions caused by the disposal of fecally soiled diapers in the landfills. Due to the nature of today's disposable diapers many, if not most, adults dispose of soiled diapers by merely tossing them in the household garbage. From there they are transported to the municipal landfill and disposed of without any treatment whatsoever. Thus, untreated fecal waste accumulates every day by the ton in municipal landfills causing a serious health hazard.

In contrast, however, the present invention provides for a disposable diaper with a separable inner sheet for flushing in a toilet or water closet where it will be transported to a treatment facility. The remaining portion of the diaper is made of biodegradable materials for landfill disposal.

The present invention, therefore, allows the fecally contaminated inner sheet of the diaper to be treated at a conventional wastewater treatment facility while at the same time providing for the disposal of the remaining diaper portion at a normal landfill. Moreover, the present invention is easy to use, convenient and effective.

Thus, the present invention provides numerous advantages over prior disposable diapers and eliminates many of the environmental and health hazards therein.

SUMMARY OF THE INVENTION

The present invention relates to an improved biodegradable disposable diaper. In its preferred embodiment, the disposable diaper comprises a removable inner sheet having a layer of liquid permeable material, a first layer of absorbant material and a first layer of moisture repellent material. Once soiled, the inner sheet of the diaper is removed and flushed for treatment at a wastewater treatment facility.

The diaper further comprises, in its preferred embodiment, a second layer of absorbant material associated with the inner sheet; a second layer of moisture repellent material associated with the second layer of absorbant material that extends beyond the inner sheet along both longitudinal and transverse planes; and a plurality of perforations formed in the inner sheet at the Peripheral coterminous points of the inner sheet and second layer of moisture repellent material.

Normally, a plurality of fastening tabs is attached to the second layer of moisture repellent material for attachment of the diaper to the infant when in use.

In the preferred embodiment of the present invention the first and second layers of absorbant material are absorbant cotton and the first and second layers of moisture repellent material are a coated paper, normally coated with a natural wax. In the preferred embodiment there is also a removal means such as a twisted paper drawstring attached along the periphery of the inner sheet.

It is well known that absorbant cotton and paper coated with a natural wax are capable of complete biodegradation within a few weeks time. Thus, the present invention is vastly superior to the plastic material normally utilized in improved diapers such as disclosed in U.S. Pat. Nos. 4,685,916 and 4,695,278. Therefore, the present invention is both an environmental and sanitary improvement over prior disposable diapers.

BRIEF DESCRIPTION OF THE DRAWINGS

A more complete understanding of the invention and its advantages will be apparent from the Detailed Description taken in conjunction with the accompanying Drawings, in which:

FIG. 5 is a schematic representation of the inner sheet of the improved disposable diaper after removal; and FIG. 6 is a schematic representation of the inner sheet of the improved disposable diaper more clearly illustrating the attachment of the removal means.

DETAILED DESCRIPTION OF THE INVENTION

Figure 1:
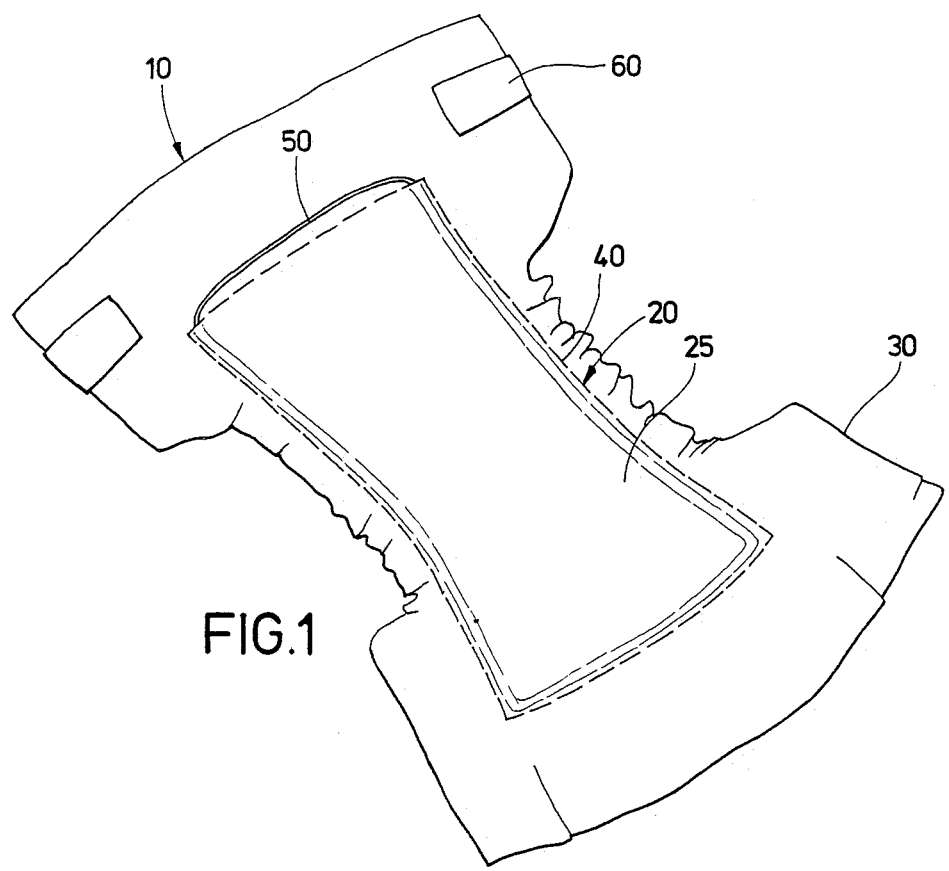
FIG. 1 is a schematic representation of the improved disposable diaper before removal of the inner sheet.

Referring now to FIG. 1, therein is shown the biodegradable improved disposable diaper 10 including the inner sheet 20 and outer biodegradable moisture repellent material 30. The outer biodegradable moisture repellent material 30 extends beyond the borders of the inner sheet 20 along both longitudinal and transverse planes. A plurality of perforations 40 are located in the inner sheet 20 at the peripheral coterminous points between the inner sheet 20 and outer moisture repellent material 30.

The inner sheet 20 also has a removal means 50, which in the preferred embodiment is a drawstring, for easy removal and disposal of the inner sheet 20. Normally such disposal is accomplished by flushing which allows for treatment of the soiled inner sheet at a conventional wastewater treatment facility.

FIG. 1 also illustrates that the improved diaper 10 may have a plurality of fastening tabs 60 in order to attach the diaper 10 to an infant during use. Such tabs 60 are conventional and well known in the art.

The inner sheet 20 has a layer of liquid permeable material 25 which allows liquids and other excrements to pass therethrough to an absorbant layer 70 directly underneath. The liquid permeable layer 25 may be made of any conventional material well known in the art such as that disclosed in U.S. Pat. Nos. 4,685,916 and 4,695,278, which disclosure is incorporated herein by reference.

Figure 2:
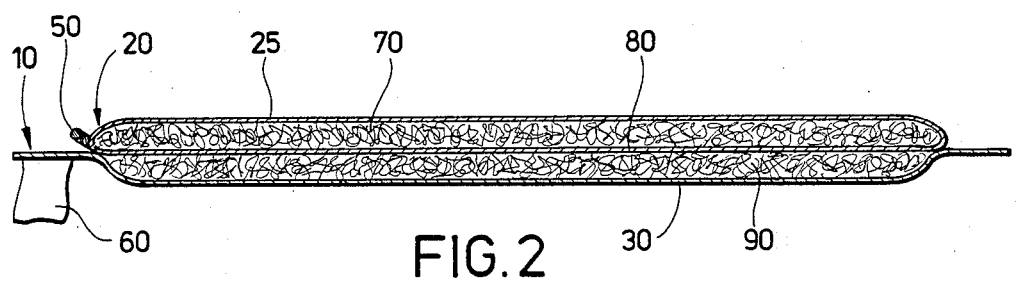
FIG. 2 is a cross sectional view of the disposable diaper before removal of the inner sheet.

FIG. 2, a cross-sectional representation of the improved diaper 10, clearly illustrates that the inner sheet 20 consist of three layers of separate material, including a liquid permeable layer 25, absorbant layer 70 and interior layer of moisture repellent material 80. The inner sheet 20 triparte arrangement is bonded and attached in any conventional and well known manner, including the use of adhesives. The absorbant material 70 may be of the artificial type such as disclosed in U.S. Pat. Nos. 4,685,916 and 4,695,278 or may be of a natural absorbant cotton or like material.

The first layer of moisture repellent material 80 may be of any biodegradable material, but in the preferred embodiment is a coated paper. The coating for the paper of layer 80 may be made of any biodegradable material, but is normally a natural wax or petroleum wax such as parafin, beeswax, lanolin, mayberry, sugar cane or carnauba.

Attached to the first layer of coated paper 80 is a second layer of absorbant material 90, also biodegradable. In the preferred embodiment the absorbant material 90 is an absorbant cotton or like material. Also shown in FIG. 2 is the outer layer of biodegradable moisture repellent material 30 and its relationship to the inner sheet 20 and absorbant material 90.

Once the inner sheet 20 has been removed, the remainder of the diaper, including absorbant layer 90 and outer layer 30, may be disposed of in any conventional manner such as tossing in the household garbage.

Figure 3:
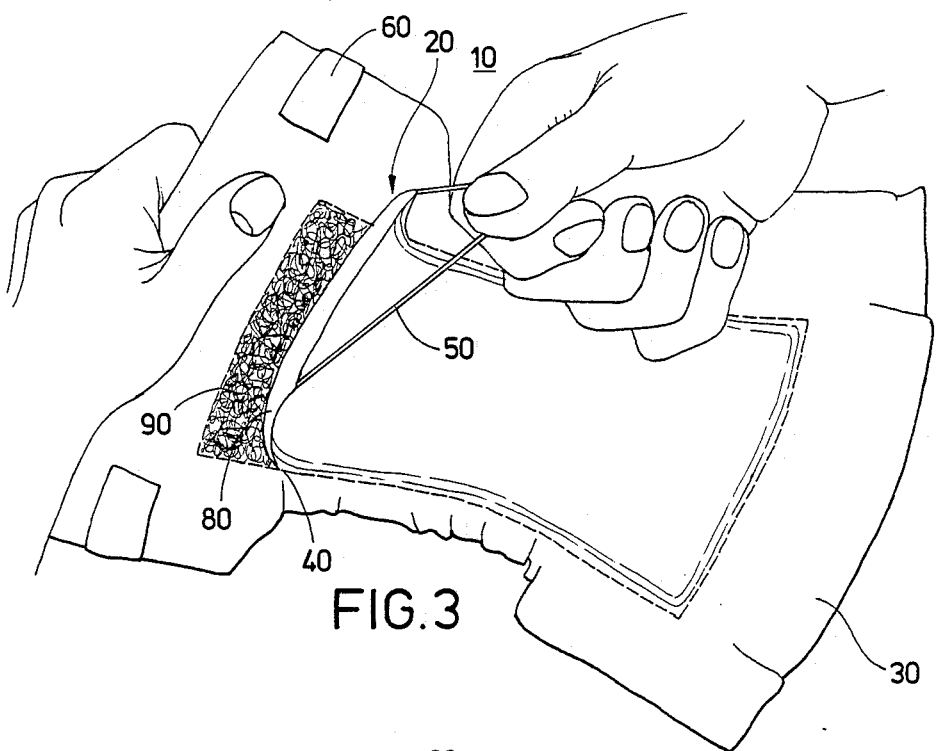
FIG. 3 is a schematic representation of the beginning stages of removal of the flushable inner sheet.

FIG. 3 illustrates the utilization of drawstring 50 to remove the inner sheet 20. The perforations 40 aid in the removal of the inner sheet 20 as drawstring 50 is pulled. After removal of inner sheet 20, the absorbant layer 90 and outer water repellent sheet 30 are disposed of in a conventional means, such as tossing in the household garbage whereas inner sheet 20 is disposed of by flushing in a toilet or water closet.

Figure 4:
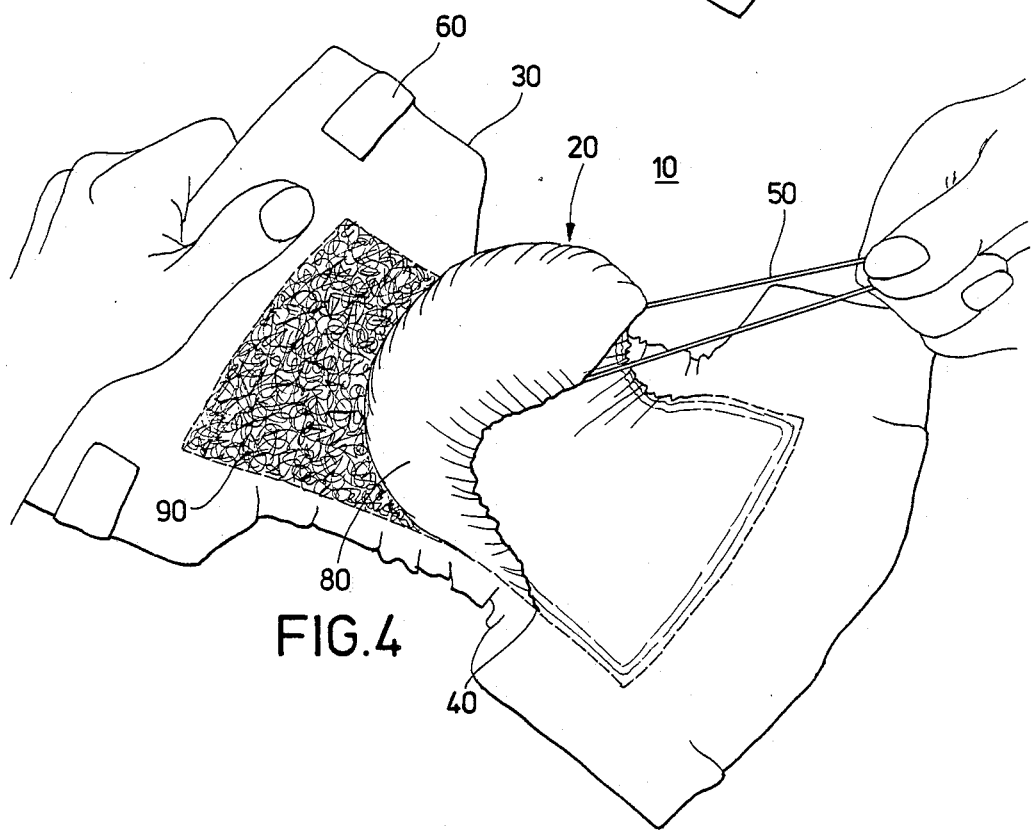
FIG. 4 is a schematic representation of the improved disposable diaper revealing the further removal of the inner sheet from the diaper.

FIG. 4 shows how the inner sheet 20 begins to bundle up upon itself as it is removed from the diaper 10. Again, the perforations 40 and drawstring 50 facilitate the bundling and removal of the soiled inner sheet 20. FIG. 5 discloses a fully removed and bundled inner sheet 20 in a configuration ready for flushing.

FIG. 6 illustrates the attachment of the drawstring 50 to the inner sheet 20 through a series of hollow channels 100 located in the periphery of the inner sheet 20. Normally the drawstring 50 is made of a twisted paper material that is easily biodegraded, but strong enough to support the inner sheet 20 when removed.

Although the inventions have been described in detail, it is to be clearly understood that the same is by way of illustration and example only and is not to be taken by way of limitation, the sphere and scope of the invention being limited only to the terms of the appended claims.

I claim:

1. Improved biodegradable disposable diaper comprising:
    a removable inner sheet having a layer of liquid permeable material, an interior first layer of absorbant material and a first layer of moisture repellant material;
    a removal means attached to the inner sheet for easy removal of the inner sheet;
    a second layer of absorbant material associated with the inner sheet;
    a second layer of moisture repellant material associated with the second layer of absorbant material and extending beyond the inner sheet along both longitudinal and transverse planes;
    a plurality of perforations in the inner sheet located at the peripheral coterminous points of the inner sheet and second layer of moisture repellant material; and
    a plurality of fastening tabs attached to the second layer of moisture repellant material.

2. An improved biodegradable disposable diaper in accordance with claim 1 wherein the first layer of absorbant material is absorbant cotton.

3. An improved biodegradable disposable diaper in accordance with claim 1 wherein the first layer of moisture repellent material is a coated paper.

4. An improved biodegradable disposable diaper in accordance with claim 3 wherein the coating on the coated paper is a natural wax.

5. An improved biodegradable disposable diaper in accordance with claim 1 wherein the second layer of moisture repellant material is a coated paper.

6. An improved biodegradable disposable diaper in accordance with claim 5 wherein the coating on the coated paper is a natural wax.

7. An improved biodegradable disposable diaper in accordance with claim 1 wherein the second layer of absorbant material is absorbant cotton.

8. An improved biodegradable disposable diaper in accordance with claim 1 wherein the removal means is a drawstring.

9. An improved biodegradable disposable diaper in accordance with claim 8 wherein the drawstring is twisted paper.

10. An improved biodegradable disposable diaper comprising:
- a removable inner sheet having a layer of liquid permeable material, an interior first layer of absorbant material and a first layer of coated paper attached to the absorbant material;
- a drawstring attached to the inner sheet along its Periphery for easy removal of the inner sheet;
- a second layer of absorbant material associated with the coated paper of the inner sheet;
- a second layer of coated paper associated with the second layer of absorbant material and extending beyond the inner sheet along both longitudinal and transverse planes;
- a plurality of perforations in the inner sheet located at the peripheral coterminous points of the inner sheet and second layer of coated paper; and
- a plurality of fastening tabs attached to the extended portion of the second layer of coated paper.

11. An improved biodegradable disposable diaper in accordance with claim 10 wherein the first layer of coated paper is coated with a natural wax.

12. An improved biodegradable disposable diaper in accordance with claim 10 wherein the second layer of coated paper is coated with a natural wax.

13. An improved biodegradable disposable diaper in accordance with claim 10 wherein the second layer of absorbant material is absorbant cotton.

14. An improved biodegradable disposable diaper in accordance with claim 10 wherein the drawstring is twisted paper.

15. An improved biodegradable disposable diaper comprising:
- a removable inner sheet having a layer of liquid permeable material, a first layer of absorbant cotton; a first layer of paper coated with a natural wax attached to the first layer of absorbant cotton and having hollow channels along its periphery;
- a twisted paper drawstring attached to the inner sheet along its periphery through the hollow channels therein for easy removal of the inner sheet;
- a second layer of absorbant cotton associated with the first layer of paper coated with a natural wax;
- a second layer of paper coated with a natural wax associated with the second layer of absorbant cotton and extending beyond the inner sheet along both longitudinal and transverse planes;
- a plurality of perforations in the inner sheet located at the peripheral coterminous points of the inner sheet and second layer of paper coated with a natural wax for easy detachment of the inner sheet; and
- a plurality of fastening tabs attached to the extended portion of the second layer of paper coated with a natural wax.

* * * * *

UNITED STATES PATENT AND TRADEMARK OFFICE
CERTIFICATE OF CORRECTION

PATENT NO.  : 4,964,857
DATED       : October 23, 1990
INVENTOR(S) : Charles Osborn It is certified that error appears in the above-identified patent and that said Letters Patent is hereby corrected as shown below:

Column 1, lines 28 and 29   —   "Permeable" should be --permeable-

Column 2, lines 34 and 35   —   "Peripheral" should be --peripheral--.

Column 4, line 28   —   "Improved" should be --An improved--

Column 5, line 12   —   "Periphery" should be --periphery--.

Signed and Sealed this

Nineteenth Day of May, 1992

*Attest:*

DOUGLAS B. COMER

*Attesting Officer*      Acting Commissioner of Patents and Trademarks